United States Patent

Blass et al.

Patent Number: 5,657,779
Date of Patent: Aug. 19, 1997

[54] METHOD AND APPARATUS FOR FORMING ELONGATE PTFE MATERIAL AND PTFE MATERIAL PARTICULARLY DENTAL FLOSS

[75] Inventors: Jacob Moses Blass, London; John Murray, Brighouse, both of England

[73] Assignee: Westone Products Limited, London, England

[21] Appl. No.: 538,127

[22] Filed: Oct. 2, 1995

[30] Foreign Application Priority Data

Oct. 3, 1994 [GB] United Kingdom ............ 9419859

[51] Int. Cl.$^6$ ............................................. A61C 15/00
[52] U.S. Cl. ..................... 132/321; 132/323; 132/324; 132/480; 132/339
[58] Field of Search ........................ 132/321, 323, 132/324, 325, 326, 327, 328, 329; 433/142, 166, 216

[56] References Cited

U.S. PATENT DOCUMENTS

| 3,953,566 | 4/1976 | Gore . | |
|---|---|---|---|
| 3,962,153 | 6/1976 | Gore . | |
| 4,208,745 | 6/1980 | Okita . | |
| 4,277,429 | 7/1981 | Okita | 264/127 |
| 4,776,358 | 10/1988 | Lorch . | |
| 5,220,932 | 6/1993 | Blass | 132/321 |
| 5,392,794 | 2/1995 | Striebel | 132/324 |

FOREIGN PATENT DOCUMENTS

| 652015B | 7/1992 | Australia | 132/321 |
|---|---|---|---|
| 0076246 | 6/1983 | European Pat. Off. . | |
| 0335466 | 10/1989 | European Pat. Off. . | |
| 0391887 | 10/1990 | European Pat. Off. . | |
| 2134133 | 8/1972 | France . | |
| 2134331 | 12/1972 | France | 132/321 |
| 1124109 | 8/1968 | United Kingdom . | |
| 1287874 | 6/1972 | United Kingdom . | |
| 1525980 | 9/1978 | United Kingdom . | |
| 1541681 | 7/1979 | United Kingdom . | |
| 2025835 | 1/1980 | United Kingdom . | |
| 2037294 | 11/1980 | United Kingdom . | |
| 2128133 | 4/1984 | United Kingdom | 132/321 |
| 2258402 | 2/1993 | United Kingdom | 132/321 |
| 2278283 | 11/1994 | United Kingdom | 132/321 |
| 92/10978 | 7/1992 | WIPO . | |

Primary Examiner—Gene Mancene
Assistant Examiner—Philogene Pedro
Attorney, Agent, or Firm—Larson & taylor

[57] ABSTRACT

An elongate PTFE material is formed by passing an unsintered PTFE tape across a heated surface in sliding contact therewith while applying tension to the tape, such that the PTFE tape, when its temperature is raised by contact with the heated surface, is longitudinally stretched with simultaneous width and thickness reduction while in contact with the surface. PTFE tapes having different properties, e.g. coefficients of friction at opposite faces can be produced. Such tapes are suitable for use as dental flosses.

33 Claims, 1 Drawing Sheet

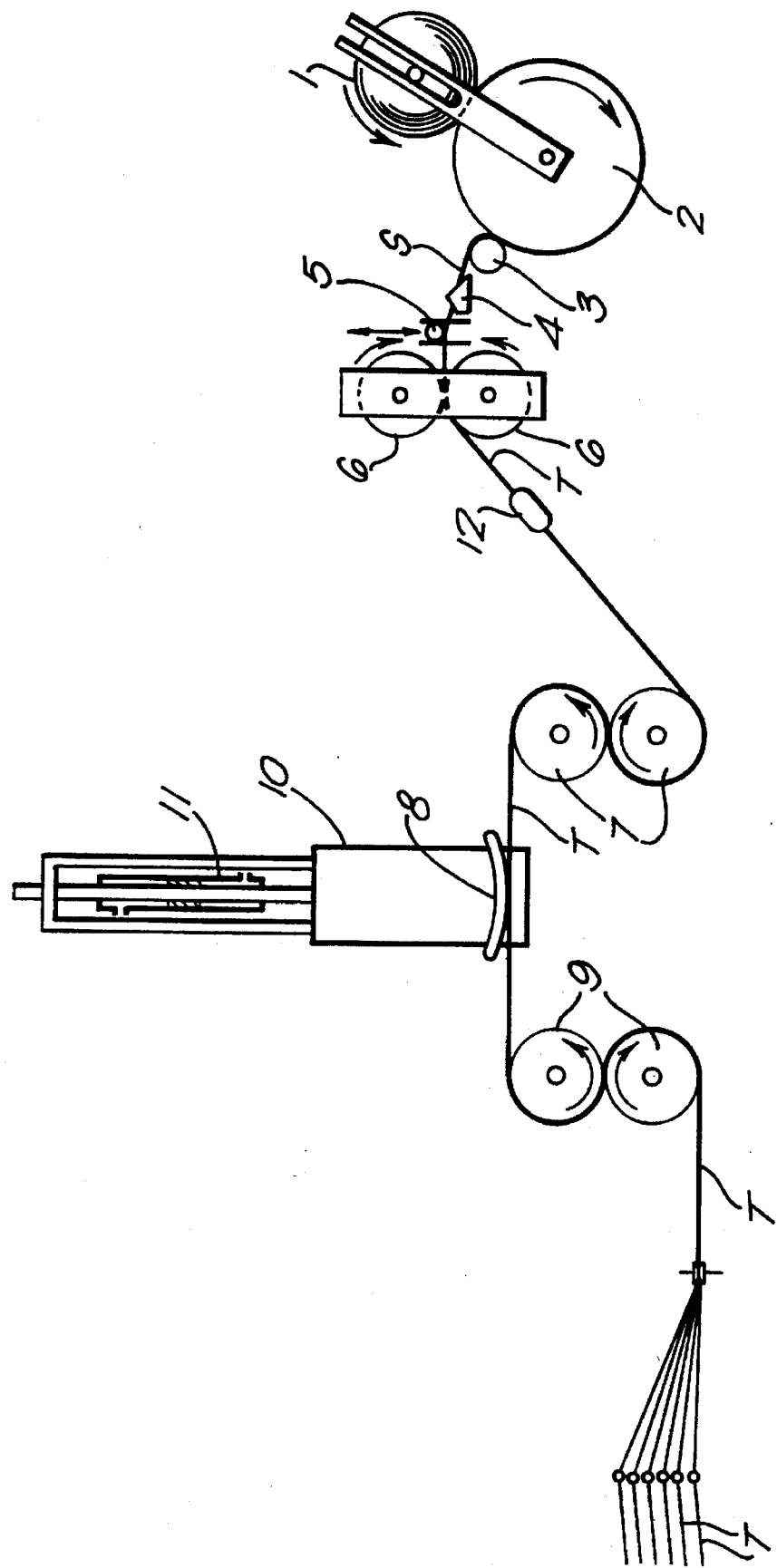

1

METHOD AND APPARATUS FOR FORMING ELONGATE PTFE MATERIAL AND PTFE MATERIAL PARTICULARLY DENTAL FLOSS

TECHNICAL FIELD

This invention relates to a method for forming an elongate PTFE material, and also to a PTFE material. The PTFE material of the invention has many possible uses, for example in or as dental floss or other dental care articles, and as a thread or yarn for sewing or weaving, e.g. to make woven filters, and as a suture. Application of the material as dental floss, or in dental flossing devices, is described more below.

BACKGROUND ART

The improvement of the strength properties of PTFE in the form of sheet, tape or rod by processes involving heating and stretching is well known. Particularly important has been the development of the process of "expansion" of PTFE by W. L. Gore & Associates, Inc. (Gore), which involves stretching an unsintered PTFE article at a high rate of stretch at an elevated temperature, to cause expansion (i.e. density reduction, with increase of porosity) of the PTFE. The isothermal expansion stage is followed by increase of temperature, with the material retained in its expanded state, to at least 327° C. which effects the phenomenon known as amorphous locking or node-locking, by the formation of amorphous regions in the PTFE which appear to lock together the fibrils of PTFE. This process is described for example in Gore's U.S. Pat. Nos. 3,953,566 and 3,962,153, where examples are given of biaxial and uniaxial stretching of films, and uniaxial stretching of rods. Sheets having two-dimensional strength, i.e. substantially equal tensile strengths in two perpendicular directions, are subjected only to biaxial stretching.

Non-contact heating of an extruded PTFE article while it is being stretched is also disclosed in GB-A-2025835.

A different process, involving sintering of the PTFE before stretching is described in EP-A-391887. GB-A-1525980 describes a process of peeling a curtain of threads from a sintered PTFE block, and stretching the thread curtain while it passes over a curved heated surface. The threads are then brought together to form a cable or yarn. The individual threads are very fine.

It is well known that unsintered PTFE articles, such as extruded tape, differ much in their behaviour in heat treatment from thermoplastic polyolefins such as polyethylene. For completeness of prior art disclosure in relation to the invention to be described below, there is also mentioned GB-A-1287874 which describes a process of producing fibres from a polymer film in which the film is fed to a combined slitting and stretching zone in which apparently the cutting device is heated. The cut fibres are stretched by taking them up from the cutting tool at a rate faster than the film feed rate. After stretching, the fibres pass over a curved guide surface, which may be heated. Although PTFE is mentioned, the only detailed example employs polypropylene film.

In GB-A-1541681, an orientable polymer strip is passed over a heated fixed metal tube, to provide a limited heating region in a stretching zone. PTFE is mentioned, but the examples disclose use of polyethylene, and the aim of the technique is to minimize the width reduction occurring on stretching while achieving high orientation of the polymer.

GB-A-1124109 discloses passing a polyolefin body over a straight pressure edge, which is heated, and stretching it so that a necking shoulder forms at the pressure edge. Biaxially oriented ribbons and tapes are obtained. Polyethylene and polypropylene are employed in the examples.

The application of expanded PTFE material as dental floss is described in U.S. Pat. No. 4,776,358, in which material obtainable from Gore in the form of tape is used to form an elongate envelope containing cleaning material. The exterior surface of this PTFE envelope is not coated.

A second dental floss made of PTFE is described in EP-A-335466. Expanded PTFE of a particular strength produced by the Gore expansion process is coated with microcrystalline wax.

Another dental floss based on PTFE not made by the Gore expansion process is described in WO 92/10978 (Westone).

The use of PTFE in dental floss is also mentioned briefly in U.S. Pat. No. 4,836,226.

It is desirable to employ, in a dental floss, a PTFE material which in use is resistant to fibrillation, i.e. the separation of fibrils from the main body of the material.

DISCLOSURE OF THE INVENTION

The present invention seeks to provide a method for the formation of an elongate PTFE material, which can be simple and employ inexpensive apparatus, while at the same time allowing selection of properties of the PTFE product. Particularly, it is desired to provide a PTFE product which reduces or avoids fibrillation in use. The product can have many uses, and can be particularly suitable for use as a dental floss, and the process can produce an elongated PTFE article of suitable dimensions for use as dental floss, avoiding the need to slit the material longitudinally after elongation. This avoids any defects which may be introduced by slitting after elongation.

According to the invention in one aspect there is provided a method of forming an elongate PTFE material, comprising passing an unsintered PTFE tape across a heated surface in sliding contact therewith while applying tension to the tape, wherein the temperature of the heated surface, the passage speed of the tape and the tension applied are such that the PTFE tape, when its temperature is raised by contact with the heated surface, is longitudinally stretched (i.e. stretched in its direction of movement) with simultaneous width and thickness reduction while in contact with the surface. This longitudinal stretching takes place at least partly when the tape is in contact with the surface, but some stretching and width and thickness reduction may continue after the contact ceases. Since the tape is usually tensioned, there also may be a small amount of stretching prior to contact with the surface.

The PTFE tape may be any unsintered tape susceptible to stretching under the conditions of the method. Preferred is an extruded tape as described below. By the term unsintered tape, we include unsintered tapes substantially unchanged in sintering state after extrusion and also tapes having some degree of sintering but which are capable of being longitudinally stretched in the method of the invention.

Preferably the method includes the step of effecting node-locking (amorphous locking) of the PTFE of at least part of the tape after longitudinal stretching. This node-locking step preferably takes place while the PTFE tape is in contact with the heated surface, but may take place subsequently. Heat may be applied subsequently to effect node-locking and/or sintering, e.g. by a further heater. Preferably the contact surface is the sole source of heat for the stretching step. When node-locking takes place in contact with the heated surface, it follows immediately after the longitudinal stretching, and it may be that these two steps are to some extent combined. The node-locking is typically effected by raising the temperature of the PTFE to its melting or sintering temperature range, i.e. to at least 327° C. and preferably to at least 346° C. After the node-locking, the PTFE element generally undergoes substantially no further longitudinal stretching.

Preferably the contact path of the PTFE tape on the heated surface is convexly curved but a flat surface may in principle be used. Preferably, this heated surface is part-cylindrical, the PTFE tape preferably passing circumferentially over the surface in a plane perpendicular to the axis.

The radius of curvature of the contact path of the PTFE tape on the heated surface is preferably in the range 100 cm to 0.3 cm.

The temperature of the heated surface can be selected within a wide range, preferably 35° to 550° C., more preferably 200° to 500° C. To achieve node-locking by the heating applied by the heated surface, its temperature should be at least 320° C.

In the process of the invention, the PTFE tape is heated mainly or entirely conductively by its one-side contact with the heated surface, so that its temperature increases as it passes across the surface. At a certain point, the PTFE reaches a temperature such that, at the tension applied at that point, it extends longitudinally, with simultaneous width and thickness, reduction. This temperature is below the melting or sintering temperature of PTFE. The thickness reduction progressively brings the bulk of the material in the cross-section, on average, closer to the heated surface, so that the temperature distribution across the cross-section may be reduced. On the other hand, the material is now moving faster, due to its longitudinal stretching. Overall, the effect is a simultaneous width and thickness reduction with longitudinal extension, i.e. a necking down of the material, at least partly while in contact with the heated surface.

It can be seen that this process is not isothermal, in that the temperature of the tape is progressively rising as it moves across the heated surface and is in most or all cases non-uniform across the thickness of the material due to the one-side contact, and furthermore the material is accelerating as it passes across the surface, due to the longitudinal stretching. Contact time with the heated surface may vary widely depending on the particular process and product, but for example is in the range of 0.5 to 10 seconds. The length extension (stretching ratio) can therefore be selected, and can be very high. Preferably in the invention, the extension (extended length/original length) is at least 10, and may be in the range 20 to 100, but it may be higher. In general, the higher the length extension the higher the tensile strength of the extended material.

The width reduction of the tape occurring in the stretching is preferably at least 50%, more preferably at least 60% and most preferably at least 70%.

As mentioned above, the node-locking or amorphous locking preferably takes place during the contact of the PTFE tape with the heated surface. Particularly in this case, the process of the present inventions appears to be self-regulating. It is surprising that the necking down of PTFE tape, as the temperature rises, does not lead rapidly to its rupture. Without wishing to be bound by theory, the present applicants believe that uncontrolled extension of the tape to rupture is prevented or controlled by one or more of (i) node-locking, (ii) sintering, (iii) cooling of the tape as it leaves the contact with the heated surface and (iv) work hardening of the tape by virtue of the stretching process.

It is, of course, possible to cause rupture of the PTFE tape, for example if the tension is too high, or the passage speed too slow so that the temperature rises too high, or the temperature is too low to permit the desired processes to occur. However, it has been found in general relatively easy empirically to establish conditions at which a particular desired process of the invention operates, and to select those conditions to achieve the desired extension (extended length/original length). It has not been necessary to monitor the tension applied. Indeed the exact value of the applied tension may not easily be obtained, because of friction losses at the contact between the PTFE tape and the heated surface, and for example the friction losses in the drive of a take-up roller. Rather, the process can be controlled by selection of appropriate values, within wide ranges, of the temperature of the heated surface, the contact length, the let-off speed and the take-up speed of the tape (i.e. input speed to the stretching step and output speed from, the stretching step) and by selection of the strength of the starting PTFE tape in one or both of the longitudinal and transverse directions. The longitudinal and transverse strengths of the starting PTFE tape, and the ratio between them, also affect the selection of the process parameters and the properties and dimensions of the stretched product.

The magnitude of the cross-sectional change, i.e. necking ratio or change of cross-sectional area, depends also on the ratio of the transverse to the longitudinal strength of the starting tape.

The starting tape (precursor tape) may have any suitable cross-section, and has a width greater than its thickness. Preferably this tape has a flat face which is the face which contacts the heated surface. The width is preferably at least twice its thickness. The thickness is preferably less than 5 mm, more preferably less than 1 mm.

As already mentioned, control of product dimensions (thickness and width) can be achieved by selection of transverse/longitudinal tensile strength ratio (which will be referred to below as "strength ratio"). Preferred for use in the invention are PTFE tapes in which the longitudinal tensile strength is not much greater than the transverse tensile strength. Such a material can be produced by selection of a suitable extrusion process, optionally with calendering, in a known manner and may be a material in which the fibrils produced by shear in the extrusion process are, to a significant extent, transversely aligned, i.e. transverse to the length direction. The strength ratio is the ratio of tensile strength in the transverse and to that in the longitudinal direction. Preferably the material used has a ratio of transverse tensile strength to longitudinal tensile strength of at least 0.2, e.g. more than 0.5. This ratio may even be greater than 1.0. There is in principle no upper limit on this ratio, and it may be, for example, up to 3. Such materials can be contrasted with those subjected to uniaxial extension in the Gore expansion process as described, for example, in U.S. Pat. No. 3,962,153, which are generally very much weaker in the transverse direction than in the longitudinal direction. The material of high strength ratio preferred for use in the invention becomes more uniaxially oriented in the stretching step of the invention, so that its fibrils become uniaxially aligned to a greater extent. Thus there is a substantial gain in longitudinal strength, but there may also be a loss of biaxiality i.e. a decrease of the strength ratio. This is in contrast to some prior art processes for polyolefin treatment in which it is attempted to retain biaxiality, i.e. to maintain transverse orientation.

In the invention, the change of cross-sectional area results from the longitudinal extension or stretching of the PTFE tape. Depending on the starting material and the process conditions, this longitudinal extension may be accompanied by an increase of porosity and reduction of density, or the porosity and density may be maintained substantially constant.

In another aspect the invention can be defined as a method of adapting the properties of an elongate unsintered PTFE tape, preferably an extruded tape, comprising uniaxially extending the tape longitudinally with simultaneous width and thickness reduction, while it is maintained in sliding contact with a heating surface which effects heating of the tape. Particularly preferred is a process where the tape has a high strength ratio as discussed above. Also preferred is node-locking (amorphous locking), while the tape is in contact with the heating surface or afterwards.

Processes for producing extruded unsintered PTFE tape for use in the invention are generally well known. The material is preferably subjected to calendering after extrusion, as is conventional, to achieve a desired thickness and properties. The extrusion die, and the calendering if employed, should be selected so as to achieve the desired strength ratio.

The term PTFE is here used, as is usual, to describe a member of a range of polymers based on polytetrafluoroethylene. For example, as is conventional, small amounts of co-monomers may be included, such as ethylene, chlorotrifluoroethylene or hexafluoropropylene, provided that the properties of the product are satisfactory.

Conventionally, PTFE is extruded with a lubricant, which is subsequently removed, for example, by heat cleaning or solvent extraction. The PTFE may, as is conventional, include one or more fillers and/or pigments. For dental floss at least, unfilled PTFE is preferred.

Preferably the contact surface used to provide the heating of the tape in the invention is stationary but the invention includes within its scope the case where the contact surface is also moving, for example at a slower speed than the lowest speed of the PTFE tape. The contact surface is preferably convexly curved with a preferred radius of curvature in the range 100 cm to 0.3 cm, and preferably provides a contact path length in the range 3 mm to 100 cm, preferably 1 cm to 50 cm.

A plurality of PTFE tapes may be passed in parallel over the heated surface, and taken up on a common take-up device e.g. roller. These parallel tapes may originate from a single wide tape which is being slit prior to contact with the heated surface. The apparatus used may therefore include slitting means for slitting a PTFE tape longitudinally, upstream of the contact surface.

The invention includes within its scope a process of producing a tape, by the extension process described above, which is subsequently sub-divided longitudinally, e.g. by slitting, to provide material of a suitable dimension for use as a dental floss.

It is found that the PTFE tape produced is resistant to fibrillation, and is amenable to coating, e.g. with wax.

The elongate stretched PTFE tape produced by the process described above may be suitable for use as it is in preparing a dental floss. Thus the product can, as a result of the stretching process, have the desired dimensions for a dental floss of tape shape made of PTFE, e.g. a width in the range of 0.5 to 4 mm, preferably 1–3 mm and a thickness in the range of 10 to 60 µm. This dental floss may be coated with wax, in a conventional manner, and the wax may include other suitable adjuvants effective in dental health care. Alternatively, the PTFE tape may be suitable for use uncoated, as discussed below. The invention thus can provide unwaxed dental floss.

The invention extends to PTFE tape produced by the method of the invention described above.

By the method described above, it has been found possible to prepare a PTFE tape having different properties at its opposite faces. Such a tape may have various uses, but in particular has been found to have satisfactory properties for use as or in a dental floss.

Therefore, according to the invention in another aspect, there is provided an integral PTFE tape having opposite faces at which the respective physical states of the PTFE material differ. Thus the properties of the opposite faces of the PTFE tape are different, and the physical state or structure of the PTFE material varies through the thickness of the tape. Thus for example, the opposite faces may differ in at least one of the following properties:

(a) reflectance, i.e. reflectivity of light. Thus one surface may be relatively matt and the other have a higher glossiness.
(b) surface roughness. One surface may be relatively smooth, compared with the other.
(c) hardness or conformability. As a result of heat treatment, one surface may be harder or less conformable than the other.
(d) coefficient of friction.
(e) peel strength after pressing onto a surface.

This means that the adhesion of the two faces of the tape, when pressed to the same test surface, is different.

This difference of a property or properties between the two faces typically results from different mechanical and/or heat treatment (e.g. degrees of sintering) of the PTFE material at the two faces. One of the faces may be substantially unsintered, while at the other face the PTFE material is at least partially sintered, and may be fully sintered and may be node-locked. The mechanical sliding of one face over the heated surface may also affect the properties. Preferably the tape is an extruded tape, and formed from an extruded, unsintered element.

The thickness of the PTFE tape having different properties or different physical states at the two faces is preferably in the range 5 µm to 1 mm, more preferably 15 to 150 µm. The tape may have a tensile strength of at least 50 MPa, preferably at least 75 MPa. In principle there is no width limitation on the tape.

The invention in another aspect therefore provides a method of making a PTFE tape having opposite faces at which the respective physical states of the PTFE material are different, the method including the step of subjecting an elongate PTFE tape to non-uniform heating across its thickness simultaneously with stretching it longitudinally to reduce its thickness and width.

We have found that a PTFE tape having opposite faces with different properties, as described above, can be particularly useful as a dental floss, and can be used as dental floss without a coating, such as a conventional wax coating. Alternatively a coating to adapt its surface properties may be applied. Particularly where one face of the tape has a relatively matt surface quality, with a coefficient of friction higher than that of the other face, the uncoated PTFE tape can be easily and conveniently gripped by the fingers of the user. A conventional PTFE tape which has a low coefficient of friction and low conformability on both sides tends to slip through the fingers of the user.

The other face of the PTFE tape having been subjected to different heat treatment, for example to node-lock or sinter it partially or wholly, the PTFE tape as a whole has sufficient strength for use as a dental floss. Preferably the uniaxial tensile strength of the tape (on average) is at least 100 MPa.

The PTFE tape may be twisted along its length, when used as a dental floss, so as to present regions of higher coefficient of friction and regions of higher conformability on each side of the floss.

The dental floss, consisting of or comprising the PTFE tape described above, can be packaged in a conventional manner, for example in a container such as a plastics material box, with an outlet aperture through which the tape can be pulled. The tape can be packed loosely in the box, or wound on a spool in the box. As is normal, the box may have a cutting means for assisting the breaking of the floss, and this may be a notch. Alternatively, the PTFE tape can be used as a floss element in a flossing device, e.g. of the type where the floss element extends between two holding arms of a frame. The preferred dimensions of the PTFE tape used as dental floss are given above.

Further advantages of the PTFE tape having opposite faces of different properties have been found to be that the tape can be wound more easily on a spool, than PTFE tape which has sintered faces at both sides, such as is produced for example by the Gore expansion process described above. If the coefficient of friction of the PTFE tape is low, it is difficult to form a coherent spool, since the tape tends to slip off the spool, e.g. when the spool is subjected to sideways forces or impact or vibration. Hitherto it has been customary to put a wax coating on the tape, before winding it into a spool. However, the tape of the present invention, without a surface coating, has been found to be easily wound into a spool which retains good coherence, and to be easily unwound from the spool also. The higher "stickability" of the tape, i.e. the adhesion between adjacent layers on the spool, apparently gives coherence to the spool. These advantages apply in use as a dental floss, where the dental floss is wound on a spool in a packaging. Furthermore, as a floss the PTFE tape can give a better grip and feel to the user, for the reasons given above, particularly when used uncoated, since there is no coating which becomes applied to the user's fingers.

BRIEF DESCRIPTION OF THE DRAWING

Embodiments of the invention will now be described by way of non-limitative example, with reference to the accompanying drawing which shows diagrammatically a process and apparatus embodying the invention. In the drawing, the single figure is a diagrammatic side view of an apparatus embodying the invention.

PREFERRED EMBODIMENTS OF THE INVENTION

In the figure, there is shown a coil 1 of extruded, unsintered PTFE sheet S. The sheet S is unwound from the roll 1 around a larger roller 2 which is driven at a predetermined speed. The sheet S is taken off the roller 2 around a small roller 3 and passes across a slitter 4 which has an array of parallel knives which subdivide the sheet S longitudinally into a plurality of parallel tapes T. Adjacent the slitter 4 is a floating roller 5 which pushes the tapes downwardly to ensure the correct position of the sheet S relative to the slitter 4. A pair of rollers 6 are driven at a predetermined speed, so as to grip the tapes T at their nip, so that the rollers 2, 6 provide tension across the slitter 4.

The parallel tapes T pass, via a guide 12 which aligns the tapes and ensures their separation, to a pair of rollers 7, which are driven at a predetermined speed to provide the predetermined let-off speed for the heating and stretching step which follows. The tapes T pass in parallel over a predetermined length of a stationary smooth convexly curved surface (radius of curvature 48 mm) of a heater 8, which contacts one side of each of the tapes. The tapes make sliding contact with the heater 8. Two heaters (A and B) have been used. Heater A is heated by a resistance heating element embedded in a ceramic matrix material of the heater, and its temperature can be set to a desired value. This heater is available from Osram Sylvania under the trade name Sylvatherm, and similar heaters are available from Vulcan Refractories (UK). Such heaters are sold for use as radiant heaters, but are employed as contact heaters in the present process.

Heaters with surfaces of other materials than ceramics may be employed. Heater B has a stainless steel skin providing the contact surface. This surface has a radius of curvature of 10 cm, a transverse length of 35 cm and a length in the running direction of 9 cm. The surface is wire-brushed to give it a satin finish rather than a mirror finish. It is clamped to a heated aluminium block.

As they pass over the heater 8, the precursor tapes are subjected to heating and stretching, so that they extend longitudinally, with simultaneous width and thickness reduction. The extended tapes then pass over the pair of rollers 9, which are also driven at a predetermined speed, higher than that of the rollers 7, the speed ratio of the rollers 7, 9 determining the length extension of the tapes T. From the rollers 9, the tapes pass to individual spooling devices, not shown, where they are wound into packages.

The heater 8 is mounted on a support 10, whose vertical position can be adjusted by a height control cylinder 11, operated pneumatically or hydraulically. This allows removal of the heater 8 from the path of the tapes entirely, and also allows adjustment of the length of the contact path of the tapes on the heater 8. In the drawing the tapes T are shown tangential to the heater surface, which is the position of minimum contact length. In operation, the contact length is longer than this minimum, and the tapes T are deflected downwardly from the horizontal position shown.

EXAMPLES 1–6

The starting PTFE element is an approximately biaxial PTFE unsintered tape, made by extrusion and calendering without filler, in which the fibrillar structure is approximately equally disposed in the lateral and longitudinal direction. The strength ratio is 0.82. Such a tape is fabricated from PTFE polymer powder by extrusion with the aid of a lubricant through a suitable die. The extruded tape is calendered to give the desired thickness and strength ratio and then treated ("degreased") by heating or solvent extraction to remove the lubricant. Such techniques are well known. A wide tape may be slit longitudinally, to provide the starting element for the present process.

The starting element has dimensions of 230 µm thickness and 13.5 mm width, 5000 tex, density 1.60 g/cm$^3$, longitudinal tensile strength of 6.7 MPa and transverse tensile strength of about 5.6 MPa.

This tape was drawn by the apparatus shown in the accompanying drawing at several different length extensions. Heater A described above was employed. The let-off speed (initial tape speed) was 12 cm/min., and the take-up speed determined the length extension (e.g. a take-up speed of 900 cm/min gives an extension of 75). The heater surface temperature was about 370° C. The contact length with the curved surface of the heater was about 3 cm. Back tension by the let-off roll is minimal, i.e. sufficient to achieve the desired contact with the heater. This process can be operated at a wide range of length extensions, and results are given in Table 1 for a range which gave particular good products for use as dental floss.

TABLE 1

| Example | Length extension (ratio) | Dimensions μm × mm | Tex | Density g/cc | Longitudinal strength MPa |
|---|---|---|---|---|---|
| — | 1 (starting tape) | 230 × 13.5 | 5000 | 1.60 | 6.7 |
| 1 | 50 | 50 × 2.3 | 121 | 1.06 | 137 |
| 2 | 55 | 44 × 2.3 | 108 | 1.08 | 181 |
| 3 | 60 | 39 × 2.2 | 97 | 1.12 | 191 |
| 4 | 65 | 36 × 2.0 | 86 | 1.18 | 214 |
| 5 | 70 | 36 × 1.9 | 82 | 1.18 | 221 |
| 6 | 75 | 34 × 1.8 | 74 | 1.17 | 235 |

Samples of these extended materials were used as dental floss without further cutting to reduce width, both uncoated and coated with wax in a conventional manner, and were found satisfactory, being very resistant to fibrillation in use and easily gripped by the user's fingers.

All of the extended PTFE tapes of Table 1 exhibited different physical states at their two faces. Particularly it was readily apparent on inspection in each case that the reflectance, smoothness, conformability and coefficient of friction was different, at the two faces.

Thus the invention can provide PTFE elements having high fibrillation resistance, particularly when the starting material for the process has a strength ratio in the range 0.2 to 3.0. As a process, the invention can achieve a high stretch ratio (length extension) with a short stretching path, by localised high temperature contact heating.

EXAMPLES 7–11

Various precursor tapes of extruded and calendered unsintered unfilled PTFE were extended by the method of the invention, using the apparatus of the drawing, to make stretched tapes of various dimensions, densities and strengths. Details of the precursor tapes, the process conditions and the product taupes are given in Table 2. Heater A was employed for Examples 7 to 11 and Heater B for Example 12.

Table 2 shows that the product properties can be selected over wide ranges, by variation of precursor material and process conditions. The products are suitable for dental floss and for uses other than dental floss.

All the tape products of Table 2 exhibit different physical structure and properties at their two faces. We classified the surface properties of the tapes generally into two characteristic surface types:

Type A: characterised by
 (i) high hardness/low conformability
 (ii) glossy surface
 (iii) low adhesive property
 (iv) low coefficient of friction Type B: characterised by
 (i) low hardness/high conformability
 (ii) matt surface
 (iii) significant adhesive property
 (iv) higher coefficient of friction than type A.

The product tape of Example 7 has two faces both of type B, though differing slightly. This is thought to be because the temperature at which stretching took place is below that associated with either node locking or sintering.

The product tape of Example 11 has two faces which are both of type A, though they differ slightly. The temperature of stretching is relatively low (compared with Examples 8, 9 and 10) but, because the precursor tape is relatively thin and the precursor tape let-off speed (input speed) and the length extension are both low, there is a longer contact time with the heater surface resulting in more uniform properties at the two faces of the product tape. Both faces have the hard and glossy appearance, associated with a sintered surface.

The product tapes of Examples 8, 9 and 10 exhibited more sharply a difference of physical states at the two faces. One face (that which contacted the heater) is of type A, while the other face is of type B.

Quantitative observations of these properties of tapes of Examples 8, 9 and 10 were as follows: Gloss:

If two parallel wound packages of any of the tapes of examples 8, 9 or 10 are compared (a) with the heater contacting face wound outermost and (b) with the heater contacting face wound innermost, an immediate difference in light reflectance and surface gloss is apparent. In particular when viewed in fluorescent lighting the surface of

TABLE 2

|  |  | Example 7 | Example 8 | Example 9 | Example 10 | Example 11 | Example 12 |
|---|---|---|---|---|---|---|---|
| Precursor Tape | Cross section (mm × μm) | 12.7 × 230 | 15.9 × 230 | 6.4 × 230 | 9.5 × 380 | 9.5 × 97 | 12.5 × 250 |
|  | Longitudinal tensile strength (MPa) | 6.7 | 6.7 | 6.7 | 2.4 | 12.5 | 7.6 |
|  | Transverse tensile strength (MPa) | 5.6 | 5.6 | 5.6 | 3.6 | 2.8 | 2.7 |
|  | Strength ratio | 0.82 | 0.82 | 0.82 | 1.5 | 0.22 | 0.36 |
|  | Tex | 4800 | 5685 | 2360 | 5685 | 1480 | 5060 |
|  | Density (g/cc) | 1.58 | 1.57 | 1.56 | 1.57 | 1.61 | 1.62 |
| Process Conditions | Tape input speed (m/min) | 0.225 | 0.295 | 0.230 | 0.170 | 0.200 | 0.500 |
|  | Tape output speed (m/min) | 11.4 | 17.0 | 21.4 | 17.0 | 7.0 | 26.0 |
|  | Extension ratio | 50.7 | 57.6 | 93 | 100 | 35 | 52 |
|  | Heater temperature (°C.) | 320 | 410 | 400 | 450 | 365 | 435 |
|  | Contact length (mm) | 40 | 45 | 15 | 60 | 40 | 65 |
| Product Tape | Thickness (μm) | 55 | 55 | 38 | 60 | 18 | 43 |
|  | Width (mm) | 2.3 | 1.9 | 0.7 | 0.75 | 1.5 | 2.5 |
|  | Tex | 93 | 100 | 30 | 62 | 40 | 100 |
|  | Longitudinal tensile strength (MPa) | 85 | 160 | 210 | 250 | 310 | 165 |
|  | Tenacity (cN/tex) | 12.0 | 16.0 | 16.5 | 18.0 | 21.0 | 18.0 |
|  | Density (g/cc) | 0.74 | 0.96 | 1.13 | 1.38 | 1.50 | 0.93 |
|  | Matrix tensile strength (MPa) | 250 | 363 | 405 | 482 | 450 | 420 | package (a) appears to be highly reflective With a high surface gloss. In package (b) by comparison, reflectivity and surface gloss are considerably reduced.

In addition, the package (a) has a slippery nature with an apparent low coefficient of friction whilst for package (b) the surface feels tacky with an apparently higher coefficient of friction.

In addition with a cross-wound package of tape, if the tape turns over during winding the difference in surface gloss can immediately be detected.

Hardness/Conformability

If these tapes are wound into cross-wound packages and a length inspected with a binocular microscope after removal from the package the following features are observed. Signs of compression by contact with the underlying tape geometry or the overlying tape geometry can be seen in the form of characteristic surface lines.

Under oblique illumination these surface lines are much more pronounced on the matt surface (B-type surface) than on the glossy surface (A-type surface). Thus the softer texture of the B-type side of the tape retains indentations caused by overlying tapes. This explains why such tapes do not fall or remove easily from packages or bobbins even when unwaxed and why hand grip can be maintained on the floss without the necessity for waxing.

Friction and adhesive properties

If a given length of tape is wrapped partly around and pressed gently into contact with a curved glass surface, such as a surface of a Pyrex beaker, and tension is applied on its free end to pull it tangentially to the curved surface, the following is observed. The matt surface (type B) strongly grips the glass surface. If the length in contact with the surface is 5–10 cm the tape can be appreciably stretched before it loses adhesion to the surface.

If the glossy surface (type A) is pressed into contact the tape can be more easily dislodged.

PTFE tapes made by processes involving sintering as described in U.S. Pat. Nos. 3,953,566 and 3,962,153 and in EP-A-391887 similarly show no tendency to adhere to the glass surface.

An extended tape made in accordance with Example 12 above has been subjected to further observation and test, as follows:

Surface Roughness

The technique employed is confocal microscopy, which is available at the Materials Science Department at the University of Surrey, England. The object under test is scanned in several planes, one plane at a time, using laser light and measuring absorption. A three-dimensional optical image is produced, and profiles of cross-sections can be generated. Gold coating of the PTFE tape was necessary in order to reveal surface details satisfactorily.

The results obtained showed that the Type A surface (as identified above) of this sample has higher values of surface roughness than the Type B surface, for each of six different roughness parameters. In summary, the Type B surface is less rough by a factor of ⅔ to ½.

This result is initially surprising, since the Type A surface is more glossy to the eye. Gloss apparently depends on other factors as well as surface profile.

Coefficient of friction

Friction was measured using a reciprocating tribology device at the Materials Department of Brunel University, England. Four superimposed layers of the tape were held on a flat steel surface by tension. A glass countersurface is reciprocated in contact with the sample, at a range of loads at the contact region. The load applied was cycled from low values to high ones and down again. The resistance to sliding is measured. Coefficient of friction (COF) was found to vary in dependence on load over parts of the load range, and behaviour was not consistent as between the load-increasing and load-decreasing parts of the cycle. Therefore the results must be treated as tentative. Nevertheless the Type A surface showed consistently lower resistance to sliding than the Type B surface. The lowest COF value for the Type A surface is 0.01 at low loads (up to 150 gf). At these loads, the COF of the Type B surface was very much higher. The Type A surface behaved more closely to what has been typically observed in earlier work on sintered PTFE.

Peel strength

Adhesion was measured between each surface of the tape and four surfaces, i.e. (i) the same surface of the tape, (ii) the other surface of the tape, (iii) a flat glass surface and (iv) a flat melamine surface, by compressing two layers of the tape between a glass microscope slide and a smooth melamine surface. A load of 8 kgf was applied for about 10 hours, at a temperature of 14°–18° C.

The peel strength was then measured. Three arrangements A, B and C were tested, to give all possible interfaces:

| Arrangement A | | |
| --- | --- | --- |
| Time of load application | | 9.5 h |
| Interface | | Peel strength (gf) |
| i | Glass/surface type B | 2.76/3.93/4.42* |
| ii | Surface type A/surface type B | 4.74 |
| iii | Surface type A/melamine | 0 |
| Arrangement B | | |
| Time of load application | | 11.75 h |
| Interface | | Peel strength (gf) |
| i | Glass/surface type A | 0 |
| ii | Surface type B/surface type B | 4.74 |
| iii | Surface type A/melamine | 0 |
| Arrangement C | | |
| Time of load application | | 12.7 h |
| Interface | | Peel strength (gf) |
| i | Glass/surface type B | 4.42 |
| ii | Surface type A/surface type A | 0 |
| iii | Surface type B/melamine | 4.42/6.44* |

* indicates multiple tests.

In conclusion the type B surface of the tape adhered to both surfaces of the tape and to glass and melamine, whereas the type A surface adhered only to the type B surface.

While the invention has been illustrated herein by embodiments, it is not limited to those embodiments, and modifications and variations may be made within the scope and concept of the invention herein disclosed.

What is claimed is:

1. A method of making PTFE dental floss, comprising passing an unsintered PTFE tape across a heated surface in sliding contact therewith while applying tension to the tape, wherein the temperature of the heated surface, the passage speed of the tape and the tension applied are such that the PTFE tape, when its temperature is raised by contact with the heated surface, is longitudinally stretched with simultaneous width reduction and thickness reduction while in contact with the surface, said width reduction being at least 50%.

2. A method according to claim 1 wherein the unsintered PTFE tape is an extruded tape.

3. A method according to claim 2 including effecting node-locking of the PTEE of at least part of said tape in its thickness direction.

4. A method according to claim 3, wherein the node-locking occurs while the tape is in contact with said heated surface.

5. A method according to claim 3 wherein the node-locking is effected by raising the temperature of the PTFE to its melting temperature range.

6. A method according to claim 1 wherein the contact path of said tape on said heated surface is convexly curved.

7. A method according to claim 1 wherein the temperature of the heated surface is in the range 35° to 550° C.

8. A method according to claim 1 wherein the PTFE tape contacts said heated surface for a time period in the range 0.5 to 10 seconds.

9. A method according to claim 1 wherein the ratio of the transverse tensile strength to the longitudinal tensile strength of the PTFE tape prior to contact with the heated surface is at least 0.2.

10. A method according to claim 1 wherein the length extension of the PTFE tape, as a result of its contact with the heated surface, is at least 10 times.

11. A method according to claim 1 wherein after the longitudinal stretching with simultaneous width and thickness reduction the PTFE tape has a tensile strength of at least 100 MPa.

12. A method according to claim 1 wherein after the longitudinal stretching with simultaneous width and thickness reduction the PTFE tape has a thickness in the range of 10 to 60 μm and a width in the range od 0.5 to 4 mm.

13. A method of making PTFE dental floss comprising adapting the properties of an elongate unsintered PTFE tape by uniaxially extending said tape longitudinally with simultaneous width reduction and thickness reduction while it is maintained in sliding contact with a heating surface, said width reduction being at least 50%.

14. A method according to claim 13 wherein the PTFE tape an extruded tape.

15. A method according to claim 14 wherein node-locking of the PTFE of at least part of the thickness of said PTFE tape is effected.

16. A method according to claim 13 wherein after the uniaxial longitudinal extension with simultaneous width and thickness reduction, the PTFE tape has a tensile strength of at least 100 MPa.

17. A method according to claim 13 wherein after the uniaxial longitudinal extension with simultaneous width and thickness reduction, the PTFE tape has a thickness in the range 10 to 60 μm and a width in the range 0.5 to 4 mm.

18. A dental floss comprising an integral PTFE tape having opposite faces at which the respective physical states of the PTFE material differ.

19. A dental floss according to claim 18 wherein the opposite faces differ in at least one of:

(a) reflectance (b) surface roughness (c) coefficient of friction, and (d) peel strength after pressing onto a surface.

20. A dental floss according to claim 18 wherein at said opposite faces the PTFE material has respectively different degrees of sintering.

21. A dental floss according to claim 20 wherein at one said face the PTFE material is substantially unsintered, and at the other said face the PTFE material is at least partially sintered.

22. A dental floss according to claim 18 wherein at one said face the PTFE material is node-locked.

23. A dental floss according to claim 18 which is an extruded tape.

24. A dental floss according to claim 18 having a thickness in the range of 5 μm to 1 mm.

25. A dental floss according to claim 18 having a tensile strength of at least 50 Mpa.

26. A dental floss comprising an integral PTFE tape having opposite faces at which the respective coefficients of friction are different.

27. A dental floss according to claim 26 in which at one face of the tape the PTFE material is substantially unsintered.

28. A dental floss according claim 26, wherein said tape is twisted.

29. A dental floss according to claim 26 wherein said PTFE tape has a tensile strength of at least 100 MPa.

30. A dental floss according to claim 26, wherein the PTFE tape has no surface coating.

31. A dental floss comprising an integral PTFE tape having opposite faces at one of which the PTFE material is unsintered and the other of which the PTFE material is at least partially sintered.

32. A dental floss according to claim 31, wherein the PTFE tape has no surface coating.

33. A method of making a dental floss comprising a PTFE tape having opposite faces at which the respective physical states of the PTFE material differ, the method comprising the step of subjecting an unsintered PTFE tape to non-uniform heating across its thickness simultaneously with stretching it longitudinally to reduce its thickness and width, the width reduction being at least 50%.

* * * * *